United States Patent
Grottel et al.

(10) Patent No.: US 8,259,757 B2
(45) Date of Patent: Sep. 4, 2012

(54) METHOD AND ANALYSIS OF SYNCHRONIZED DATA TRAFFIC OF A PACKET AND ADDRESS-ORIENTED DATA NETWORK AND CONFIGURATION OF SUCH A DATA NETWORK FOR THE IMPLEMENTATION OF THE METHOD

(75) Inventors: Joachim Grottel, Lauf (DE); Harald Karl, Fürth (DE); Friedrich Lindner, Erlangen (DE); Andreas Tröltzsch, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 329 days.

(21) Appl. No.: 12/593,998

(22) PCT Filed: Mar. 27, 2008

(86) PCT No.: PCT/EP2008/053606
§ 371 (c)(1),
(2), (4) Date: Sep. 30, 2009

(87) PCT Pub. No.: WO2008/119722
PCT Pub. Date: Oct. 9, 2008

(65) Prior Publication Data
US 2010/0118896 A1  May 13, 2010

(30) Foreign Application Priority Data

Mar. 30, 2007  (DE) .................. 10 2007 015 452

(51) Int. Cl.
*H04J 3/06* (2006.01)
(52) U.S. Cl. ..................... 370/503; 370/412
(58) Field of Classification Search .. 370/395.7–395.72, 370/401, 412–420, 503
See application file for complete search history.

(56) References Cited

U.S. PATENT DOCUMENTS

| | | |
|---|---|---|
| 2006/0114831 A1 | 6/2006 | Buduma et al. |
| 2006/0143512 A1* | 6/2006 | Jia et al. ............... 714/13 |
| 2007/0067450 A1 | 3/2007 | Malloy et al. |
| 2007/0268931 A1* | 11/2007 | Shaikli ............... 370/468 |
| 2008/0259935 A1 | 10/2008 | Grottel et al. |

* cited by examiner

*Primary Examiner* — Ricky Ngo
*Assistant Examiner* — Kan Yuen
(74) *Attorney, Agent, or Firm* — Schiff Hardin LLP

(57) ABSTRACT

In a method and network for the analysis of synchronized data traffic, at least one network participant stores sent and/or received data packets in a mirror memory, and the data in the respective mirror memories are frozen and made available for evaluation via the entire data network, upon the occurrence of a trigger event in at least one of the active network participants, while maintaining the synchronized data traffic.

21 Claims, 3 Drawing Sheets

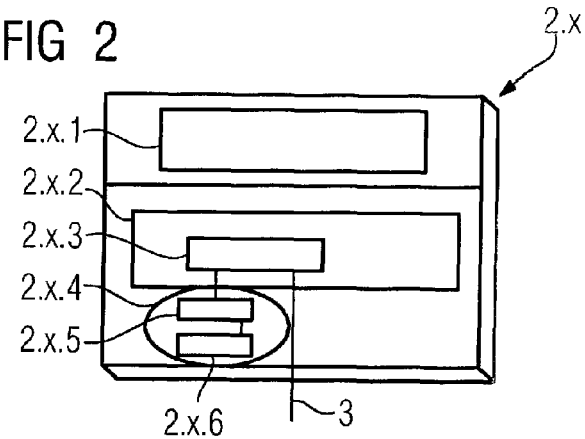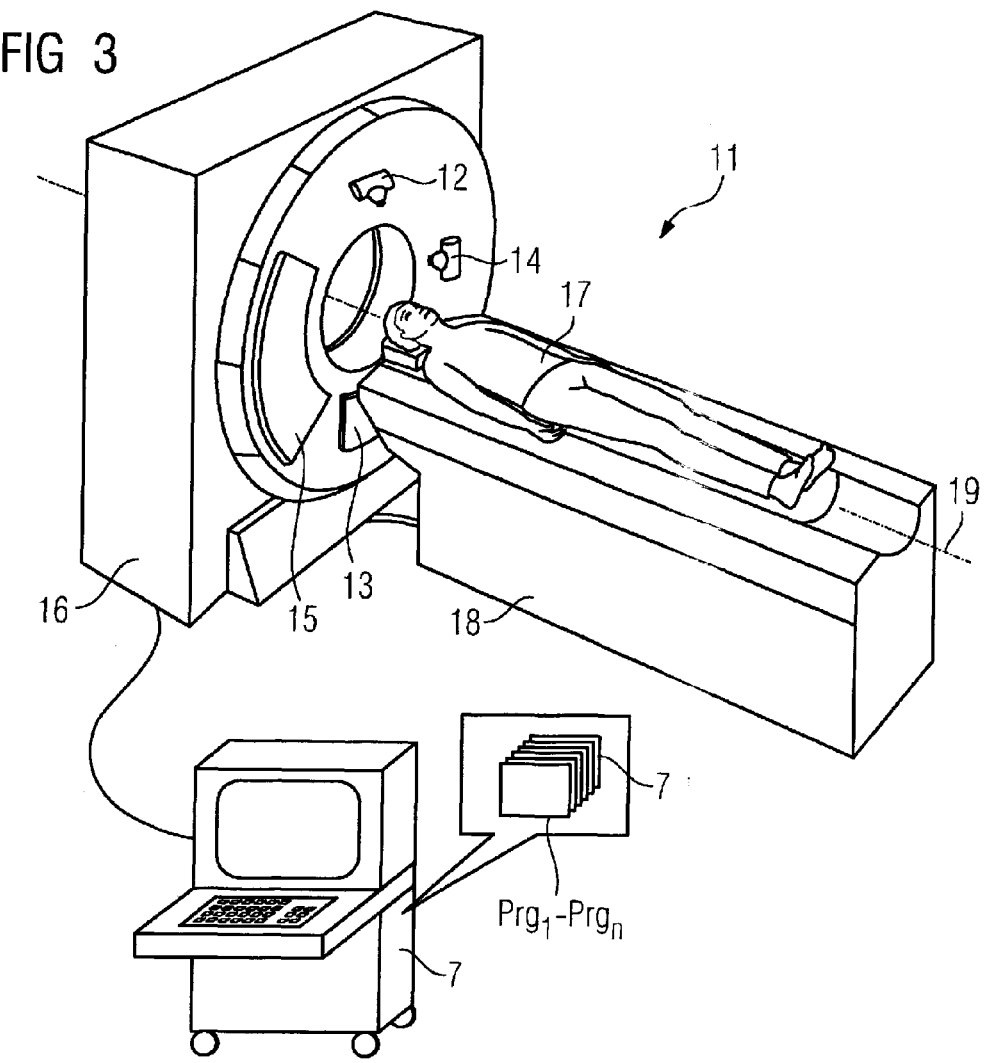

METHOD AND ANALYSIS OF SYNCHRONIZED DATA TRAFFIC OF A PACKET AND ADDRESS-ORIENTED DATA NETWORK AND CONFIGURATION OF SUCH A DATA NETWORK FOR THE IMPLEMENTATION OF THE METHOD

BACKGROUND OF THE INVENTION

1. Field of the Invention

The present invention concerns a method for the analysis of a synchronized data traffic of a packet-based and address-based data network with a number of data-generating and/or data-receiving network participants that can respectively be addressed by individual network addresses, wherein the data network synchronizes received data packets and known transmission and processing times using receipt points in time, and the data transmissions ensue synchronized with the data traffic.

Furthermore, the invention concerns a network for data and signal transmission with multiple network participants connected among one another, which participants respectively have different network addresses, wherein every network participant has transmission and reception modules in which data packets to be sent via the data network are generated and received data packets are processed, and the transmission and reception modules have synchronization modules that mutually synchronize the network participants using reception points in time of received cells and known transmission and processing times, wherein the transmission modules are fashioned such that they transfer the data packets in a synchronized manner in the data network.

2. Description of the Prior Art

The network described above is generally known. An example is described in DE 10 2005 008 503 B3. This document discloses a network for data and signal transmission that has multiple end devices as well as one or more switching stations as network components. The network components have transmission and reception modules; the transmission modules send the data to be transferred and digitized signals assembled into lines. The lines are generated with a header in which an item of connection information about at least one transmission or relaying destination of the data is incorporated. The network components have synchronization modules that mutually synchronize the network components using reception points in time of received lines and known transmission and processing times; and the transmission modules are fashioned such that they transfer the lines synchronously via the one or more switching stations.

Furthermore, general diagnostic tools for the data traffic are known. These diagnostic tools are normally connected to the network via special adapters that conduct the data acquisition and output the results to a PC. Such diagnostic tools are, however, not usable across the network, or cannot be controlled and programmed across the network because they require a special access mechanism to the freely programmable circuits contained there and a special software to use this.

Moreover, a significant problem of these known diagnostic tools is that they lead to an altered temporal behavior of the network participants that are observed as soon as the data streams of interest are recorded and analyzed. Due to this altered temporal behavior, significant problems with the timing within the network additionally result in time-synchronized networks.

A network apparatus for packet data networks is known from United States Patent Application Publication No. 2006/0114831 A1. To analyze the data traffic, the transferred data are observed in that these data are mirrored to another port without the data traffic thereby being negatively affected.

SUMMARY OF THE INVENTION

An object of the present invention is to provide a method for analysis of a synchronized data traffic of a packet-based and address-based data network and a network for synchronized data and signal transmission with multiple network participants connected among one another, the method and network enabling a data flow analysis to be conducted without interfering with the synchronized data traffic, and with which it should be possible to reconstruct the timing of the data traffic at the respective network participants from the analyzed data.

The invention is based on the insight that, in a time-synchronized data network, it is possible to equip all or at least multiple network participants with an integrated diagnosis tool which—in parallel with the incoming and outgoing data and digital signals—serially deposits these data or digital signals in a memory (for example with the use of a dual port RAM) without the actual data traffic across the data interface of the respective network participant being negatively affected. Given the occurrence of an arbitrarily predetermined or configurable trigger event, the logs of the data traffic stored up to this point in time are frozen in order to be read out later, either at the specific request of or automatically from another network address. Given the occurrence of this trigger event, all analyzers active on the network are stopped via the network so that their mirror memories contain data of the same time segment, but at different points of the network.

If the data network that is used is a time-synchronized data network (for example as described in DE 10 2005 008 503 B3), a precise knowledge exists about the timing of the data sets of the respective network participants that are to be sent or to be received. Moreover, the data stored in the mirror stores are provided with a time stamp. These time stamps are synchronous within the complete network. The timing can be reconstructed using the transmitted memory contents of the mirror memory of the diagnostic tool in which the data sets have been cached in parallel. In this way it is possible to centrally analyze the entire data traffic of a data network and detect possible errors in the data transmission.

The analyzer includes a trigger unit and a mirror memory. A data filter can additionally be used that allows all data or only data with a specific feature (for example information in the header of the transmitted data packet) to be written into the subsequent mirror memory.

The trigger unit is configurable, i.e. it can trigger at specific features in the acquired data, for example greater than/less than/equal to a specific value. Both the filter and the trigger unit can be fashioned so as to be configurable over the data network itself.

It is particularly advantageous for the diagnostic module to be implemented in what is known as a "Field Programmable Gate Array" (FPGA). It is thereby also possible to program this FPGA through a corresponding remote control and, in addition to the already configurable trigger events, to predetermine additional, arbitrary trigger events at which the freezing of the cached data occurs.

The method for the analysis of a synchronized data traffic and a corresponding network for the implementation of this method in accordance with the invention are based on these basic insights.

According to the invention, a method for the analysis of a synchronized data traffic of a packet-based and address-based data network with a number of data-generating and/or data-receiving network participants, respectively with individual network addresses, the data network synchronizes received data packets and known transmission and processing times using reception points in time, and the data transmissions ensue synchronously with the data traffic. At least one network participant records data packets sent by it via the data network in parallel with the data transmission and/or data packets received by it for internal data processing in at least one electronic memory module (=mirror memory), freezes its mirror memory upon the occurrence of a trigger event of the at least one network participant, and provides all data frozen in its mirror memory for evaluation via the network while the synchronized data traffic remains unaffected.

It is advantageous for not only a portion of the network participants, but optimally all network participants to mutually store their data traffic in parallel so that the entire network traffic can also actually be read out upon the occurrence of the corresponding trigger event.

The provision of the frozen data of the mirror memory can ensue, for example, by the frozen data being specifically retrieved from each of the at least two network participants. The possibility also exists for each of the at least two network participants to transmit the content of its mirror memory to a specific network address in the data network independently or upon request. Such a network address can be transferred with the request, for example, or a predetermined, hard-set network address can be used for this purpose. The term "network address" is used herein for a corresponding apparatus that has a specific network address in the data network. If and when a connection of the data network described herein exist with an external network (for example an internet or an intranet), the network address to which the data are transmitted can also be located at a remote data processing apparatus, possibly even on the Internet. A remote diagnosis of complex systems is thereby possible without any problems, for example.

The freezing of the mirror memory can occur by new data no longer being written into the mirror memory and by the present data remaining unchanged at least up until transmission. Naturally, the possibility also exists to specifically erase the data after a transmission, or through an external command, or automatically via an internal process.

In this context it is also noted that the mirror memory is advantageously designed such that the most recent data that are input respectively remain in the memory while, upon reaching a specific amount of data, the oldest data are discarded. In this way a data overflow in the mirror memory does not occur, and the most recent data (thus the last data traffic that occurred) are respectively transferred upon the occurrence of the trigger event.

Furthermore, it is advantageous when the data stored in the mirror memories respectively receive time stamps that are synchronous within the entire network. The stored data are given a unique temporal association that significantly facilitates a later evaluation.

Moreover, a filter that either writes all data or selects the data that are written into the mirror memory according to a specific criterion within a header of the observed data packets (for example according to the connection information) can be placed before the mirror memory in a particularly advantageous manner. Thus only data classified as relevant are stored, and the mirror memory is not overfilled with insignificant data.

Any electronic end devices that form a data source and/or a data sink can be used as network participants. For example, if an application in a computed tomography system is considered, these can be the generator and radiator of the system, for example, which can read out signals from their control circuits at any time with the aid of the integrated diagnostic tool (IDT). This is particularly helpful when disruptive effects occur in the system due to high voltage spikes. These high voltage spikes can be used as a trigger condition for the stopping of the mirror memory in order to in this way analyze the prior history of this disruption in the complete system.

Switching stations that operate the network nodes can also be used as network participants. For example, if a star network is used, such a switching station represents the center of such a star so that the communication between the individual network participants proceeds via such a switching station (a "switch").

Furthermore, a dual port RAM in connection with an FPGA (freely programmable gate array) can be used for parallel storage of the incoming/outgoing data traffic of the network participants. Such an FPGA has the advantage that—along with the trigger events that have already been configured—additional different trigger events to which the system responds with a freezing of the memory contents can be programmed from an external location (relative to the respective network participant).

Moreover, it can for example hereby be achieved that, given the occurrence of a specific event, the data of the mirror memory are sent to a specific network address, and given the occurrence of a different trigger event the data of the mirror memory are sent to a different network address. It is also possible to program the FPGA so that the trigger event is the concurrence of multiple individual events in a specific time frame. The most diverse logical links and specifications are possible.

Furthermore, it is advantageous for the switching points located in the network also be treated as network participants and for their data streams to be protocolled and handled in parallel corresponding to a network participant. It is useful for a switching point to have a number of data inputs and outputs and for a corresponding mirror memory to be provided for at least one (but better every) data input and data output so that, upon readout of the corresponding mirror memories, it can in retrospect be clearly established via which data interface the stored data were communicated.

In principle, the method described above is possible for a number of applications, but it is particularly advantageous to use this method for the data and/or signal exchange between individual networked components within a tomographical system, advantageously a computed tomography system.

Corresponding to the method described above, the invention also encompasses a network for data and signal transmission with multiple network participants connected among one another which respectively have different network addresses, wherein every network participant has transmission and reception modules in which data packets to be sent via the data network are generated and received data packets are processed. Furthermore, the transmission and reception modules has synchronization modules that mutually synchronize the network participants using reception points in time of received cells and known transmission and processing times; and the transmission modules are fashioned such that they transfer the data packets synchronously in the data network. The improvement of this network according to the invention is that at least one network participant has an electronic memory module (=mirror memory) that is connected in parallel with a data input and output, wherein at least a portion of the data packets going out and coming in via the data network is recorded in the mirror memory in parallel with the additional processing. A detection that detects a trigger event is provided that, in the case of the positive detection of the trigger event, freezes the mirror memory. A transfer unit that transfers the data frozen in the mirror memories via the network is provided that leaves the synchronized data traffic unaffected.

It is advantageous for the at least one network participant in the data traffic to have a dual port RAM with which the incoming and outgoing data are stored in the mirror memory in parallel with the data traffic.

It is furthermore advantageous for at least a portion of the network participants to be electronic end devices that form a data source and/or data sink.

Furthermore, at least one switching point (=switch) for the data traffic can be provided in the network structure.

Furthermore, it is particularly advantageous, given the presence of such a switch, for at least one switch for at least one data input/output to have at least one electronic memory module (=mirror memory) that is connected in parallel with a data input and output, with at least a portion of the data packets going out and coming in via the network being recorded in the mirror memory in parallel with the additional processing. The at least one switch has a detector that detects a trigger event which, in the case of the positive detection of the trigger event, freezes the mirror memory. A transfer unit transfers the data frozen in the mirror memory via the network and leaves the synchronized data traffic unaffected.

This switch can have a dual port RAM at least are data input/output, with which memory the incoming and outgoing data are stored in a mirror memory in parallel with the data traffic without disrupting the actual data traffic.

To unburden the mirror memory, a filter can also be provided that pre-selects the data to be stored in the mirror memory. Such a filter can be configurable via the network or can also be designed to be freely programmable.

The detector that triggers a trigger event can, for example, be an FPGA (=freely programmable gate array) or at least can contain such a component.

BRIEF DESCRIPTION OF THE DRAWINGS

FIG. 2 schematically illustrates an embodiment for a design of a network participant in the network of FIG. 1.

FIG. 3 schematically illustrates an x-ray computed tomography system with an integrated network according to the invention.

DESCRIPTION OF THE PREFERRED EMBODIMENTS

Figure 1:
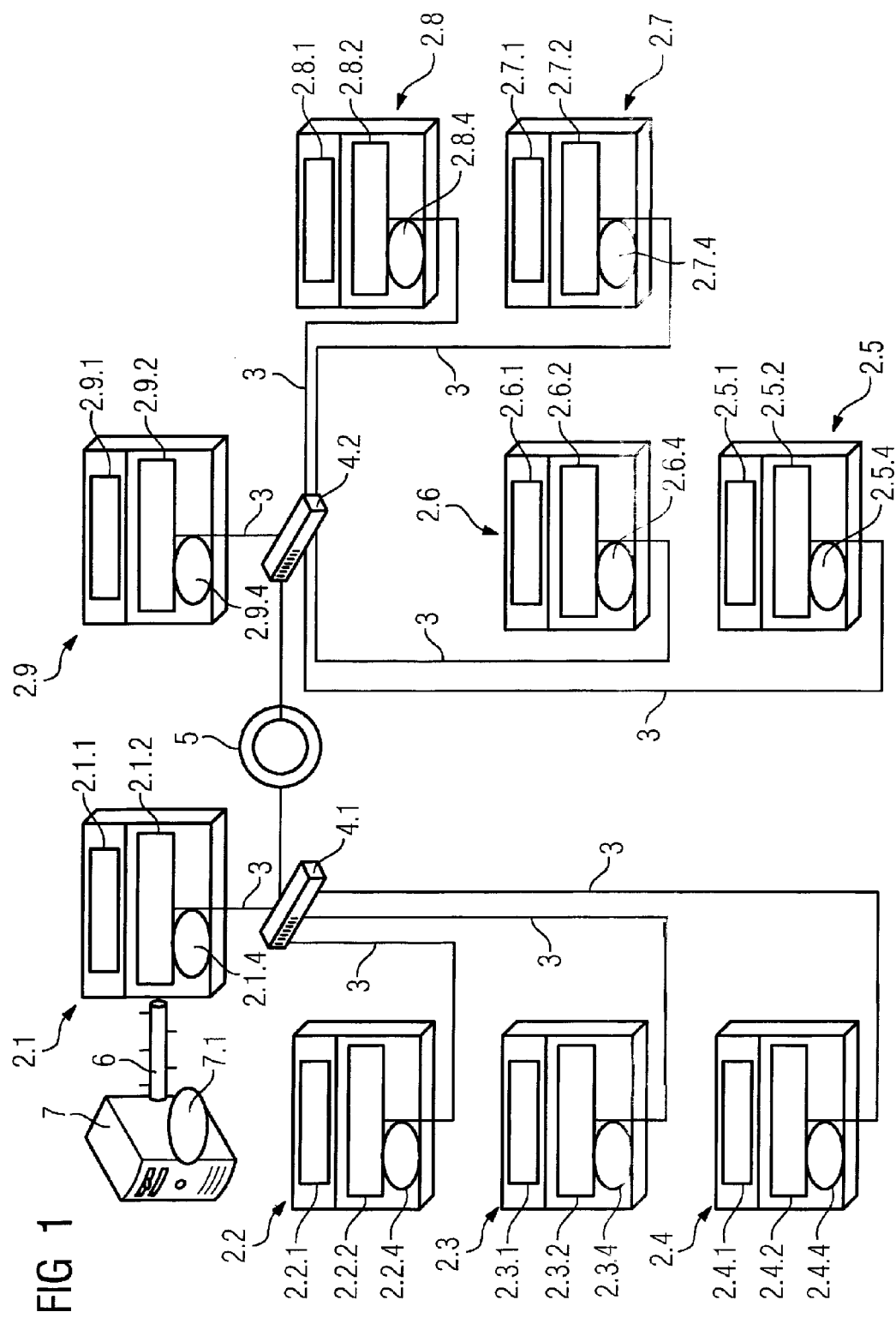
FIG. 1 schematically illustrates a network constructed and operating in accordance with the present invention.

FIG. 1 shows a tomographical overview representation of a data network 1 according to the invention, here in the example of a data network of a computer tomography system. The data network 1 is composed of ten network end components 2.1 through 2.10 in total, wherein nine network end components are directly connected with the temporally synchronized network in the CT system while a host computer 7 is additionally connected via an Ethernet 6 with the network end component 2.1, which here acts as a gateway for the actual data network. The network end components 2.1 through 2.4 represent examples of the network end components in the stationary region of the computer tomography system while the network end components 2.5 through 2.9 likewise represent examples of the network end components in the region of the rotating gantry. The explicit design of the individual network end components is shown later.

The individual network end components 2.1 through 2.4 are connected with a switch 4.1 in a star topography. The switch 4.1 is connected with a second switch 4.2 in the rotating part via a slip ring 5, which second switch 4.2 in turn provides for the network end components 2.5 through 2.9 in the gantry. The individual network lines are provided with the reference character 3.

The individual network end components are: what is known as a Universal Master Stationary Component (=UMAS) 2.1; a receiver component 2.2; a generator in the stationary part 2.3; and the patient bed 2.4. Arranged in the rotating part are: the Universal Master Rotationary Component (=UMAR) 2.9; the controller of the x-ray tubes 2.8; the controller of the collimators 2.7; the generator in the rotating part 2.6; and the detector management system of detectors A and B 2.5.

From the host computer 7 connected via the Ethernet connection 6, it is possible with the aid of the IDT front end (=integrated diagnostic tool front end) 7.1 installed there to poll the IDT back end, to configure this and to evaluate the transmitted memory contents of the mirror memory of the IDT back end in the network end components. Via the configuration of the IDT back end, the desired trigger events can be programmed in upon whose occurrence the mirror memories are frozen and output to the host computer 7 as described in the preceding.

The principle design of the individual network end components is shown in FIG. 2. This shows an arbitrary network end component 2.x that contains an application 2.x.1, thus the actual apparatus of the network end component. Arranged below this is a transport layer 2.x.2 that possesses a dual port RAM 2.x.3. The dual port RAM 2.x.3 is therefore able to act on the one hand as a data interface going out to the network line 3, and at the same time to relay the incoming and outgoing data signals in parallel to the IDT back end 2.x.4. The IDT back end 2.x.4 consists of a mirror memory 2.x.5 and a configurator 2.x.6 that is normally formed by an FPGA and, for example, can be controlled by the host 7 with the IDT front end application running therein.

In addition, an additional filter can be attached between the dual port RAM 2.x.3 and the mirror memory 2.x.5, which filter initially selects the data to be stored in the mirror memory 2.x.5 according to criteria that are predetermined, configured or programmed as needed. The storage capacity of the mirror memory can be significantly more effectively used.

It is noted that multiple analyzers (IDT back ends) 2.x.4 can also be provided in the individual network end components without leaving the scope of the invention.

FIG. 3 shows a 3D view of an x-ray CT system 11 according to the invention, consisting of a gantry housing 16 with the gantry located therein with two x-ray tubes 12, 14 and the opposite detector systems 13, 15; furthermore, the patient bed 18 which can displace the patient 17 in a controlled manner through an opening in the gantry housing along the system axis 19 around which the gantry rotates. Moreover, a host computer 7 is shown with a schematically shown memory content in which programs $Prg_1$ through $Prg_n$ are located, wherein one of these programs also provides the IDT front end 7 which operates the integrated diagnostic tools according to the invention in the individual network end components of the CT system 11 for control and polling and provides a corresponding working interface at the host computer 7.

Figure 4:
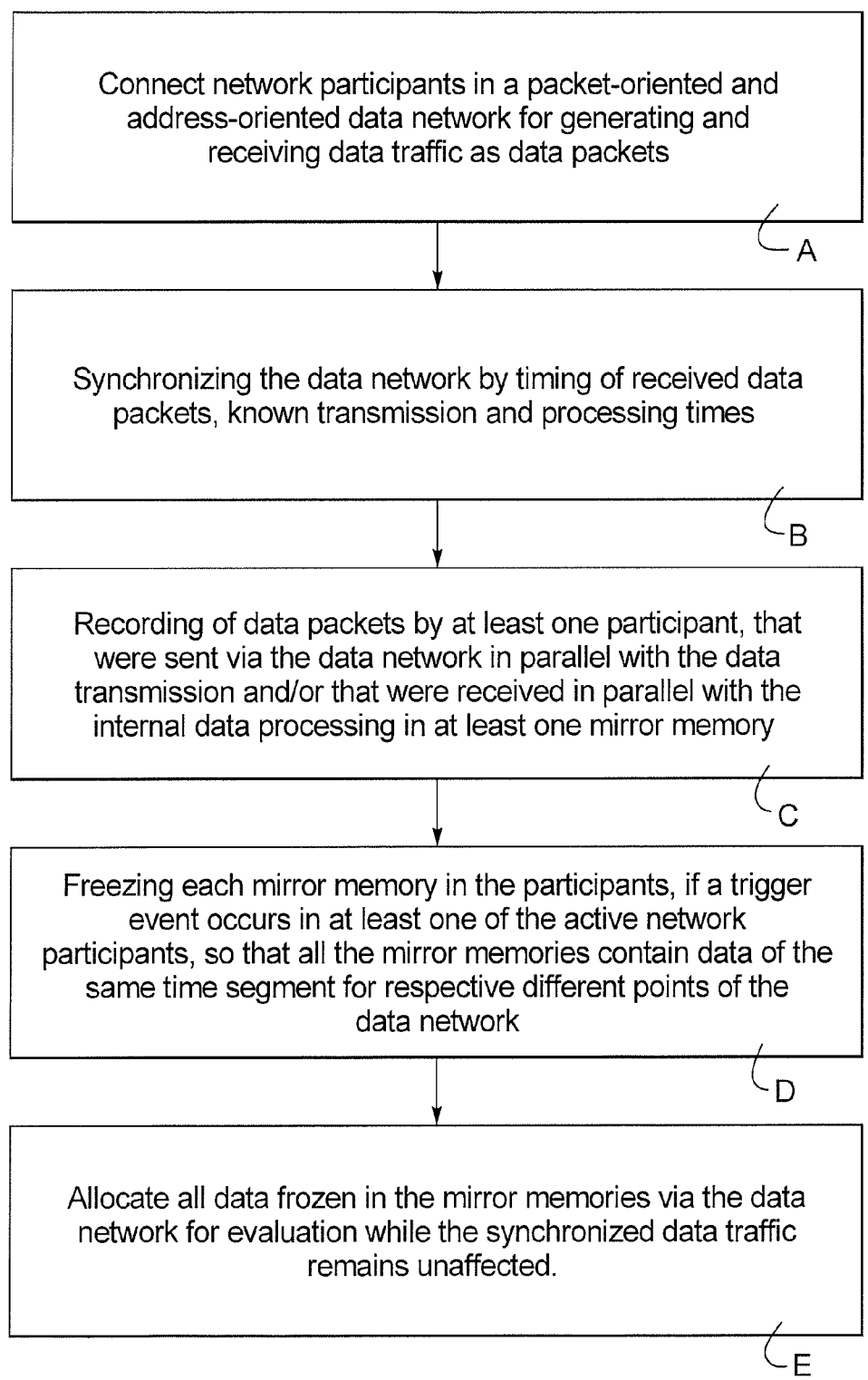
FIG. 4 is a flow chart of the basic steps in the method according to the invention.

The basic steps in accordance with the invention are shown in FIG. 4. In step A, network participants with individual network addresses are connected in a packet-oriented and address-oriented data network in order to generate and receive data traffic. In step B, the data network is synchronized dependent on the timing of received data packets, and known transmission and processing times. In step C, in a mirror memory, data packets are recorded that were sent via the network in parallel with the data transmission, and/or that were received in parallel with the internal data processing. In step D, if a trigger even occurs in at least one of the network participants, the mirror memory thereof is frozen, and all other mirror memories in the respective data participants are frozen so that all of the mirror memories contain data of the same time segment for respective different points of the data network. In step E, all of the data frozen in the respective mirror memories are transferred for evaluation, while the synchronized data traffic remains unaffected.

In summary, the invention makes use of a synchronous real-time network as a basis for an integrated diagnostic tool (=IDT). The IDT is composed of one or more mirror memories that record the real data traffic in real time without having a temporal effect on the system and can be stopped and read out as needed manually or due to the occurrence of a trigger event in a fully time-synchronized manner within the entire system. The advantage of this system is that the diagnostic data can analyze a close time correlation as this would not be possible at all without a time-synchronized system and would only be possible to a limited extent with a time-synchronized system but without IDT.

An IDT is thus operated as an integral component of the network participant (end participant or switch). All IDTs within this network are connected with one another via the network itself and are controlled via this, i.e. configured, started and stopped (for example by means of a trigger event) in an IDT. They thus operate synchronously with one another distributed across the entire network. In this way the data traffic within the network can be recorded at any point at the same time and can subsequently be analyzed.

Although modifications and changes may be suggested by those skilled in the art, it is the intention of the inventors to embody within the patent warranted heron all changes and modifications as reasonably and properly come within the scope of their contribution to the art.

We claim as our invention:

1. A method for analysis of a synchronized data traffic of a packet and address-oriented data network, comprising: a plurality of data generating and/or data-receiving network participants, respectively with individual network addresses or other individual identification features, wherein the data network synchronizes received data packets and known transmission and processing times using receipt points in time, and data transmissions ensue synchronized with the data traffic, said method comprising:
 in mirror memory in at least one network participant, recording data packets that said at least one network participant has sent via the data network in parallel with the data transmission and/or data packets that said at least one network participant has received in parallel with an internal data processing;
 upon an occurrence of a trigger event in at least one of the active network participants, in each of the network participants equipped with a mirror memory, freezing the mirror memory of that network participant to cause each mirror memory to contain data of the same time segment for respective different points of the data network; and
 providing all data frozen in the respective mirror memories via the data network for evaluation while the synchronized data traffic remains unaffected.

2. A method according to claim 1, comprising providing the frozen data of the mirror memory by retrieving the frozen data from each of the at least two network participants.

3. A method according to claim 1, comprising providing the frozen data of the mirror memory by each of the at least two network participants transmitting the content of its mirror memory to a specific network address independently or upon request.

4. A method according to claim 1 freezing the mirror memory by no longer writing new data into the mirror memory and present data unchanged at least up until transmission.

5. A method according to claim 1, comprising time stamping the data stored in the mirror memories.

6. A method according to claim 1, comprising selecting data that are written into the mirror memory according to a predetermined criterion in a filter before the mirror memory.

7. A method according to claim 1, comprising continuing storage of the input/output data transmission of the data frozen in the mirror memory.

8. A method according to claim 1, comprising connecting at least electronic end devices that form a data source and/or data sink to said network as network participants.

9. A method according to claim 8, comprising also connecting switching stations to said network as network participants.

10. A method according to claim 1, comprising employing a dual port RAM in connection with a freely programmable gate array (FPGA) for parallel storage of the incoming/outgoing data traffic of the network participants.

11. A method according to claim 1, comprising communicating conditions for the trigger event to freeze the mirror memory of a network participant to the other network participants and automatically configuring the network participant.

12. A method according to claim 1, comprising treating switching points located in the data network as network participants.

13. A method according to claim 1, comprising connecting components within a tomographical system to said network as network participants.

14. A network for data and signal transmission, comprising:
 multiple network participants connected among one another that respectively have different network addresses or another individual identification feature;
 every network participant comprising a transmission unit configured to generate data packets to be sent via the data network and a reception unit configured to receive data packets at respective reception points in time and to process received data packets;
 each transmission unit and each reception unit being configured to mutually synchronize the network participants according to the reception points in time, at the respective reception unit, of received data packets and known transmission and processing times, and the transmission units are each configured to transfer the data packets synchronously in the data network;
 each network participant comprising at least one mirror memory connected in parallel with a data input and/or output thereof, wherein at least a portion of the data packets that are incoming and outgoing via the data network is recorded in the mirror memory in parallel with the processing in the reception unit of that network participant;
 at least one network participant comprising a processing unit that configured to detect a trigger event and, upon detection of the trigger event, to freeze the mirror memory at said at least one network participant and to freeze the respective mirror memories of all other participants located on the network to cause all of the respective mirror memories to contain data of the same time segment for respective different points of the data network; and a transfer unit configured to transfer the data frozen in the mirror memories via the network while leaving the synchronized data traffic unaffected.

15. A network according to claim 14, wherein the at least two network participants in the data traffic each comprise a dual port RAM in which the incoming and outgoing data are stored in the respective mirror memories of said at least two network participants in parallel with the data traffic.

16. A network according to claim 14, wherein at least a portion of the network participants are electronic end devices that form a data source and/or data sink.

17. A network according to claim 14, wherein said network participants are connected in a network structure comprising at least one switch for the data traffic.

18. A network according to claim 17, wherein said at least one switch comprises a dual port RAM at least on data input/output thereof, said RAM storing the incoming and outgoing data are stored in a mirror memory in parallel with the data traffic.

19. A network according to claim 14 wherein each network participant comprises a filter that selects data to be stored in the mirror memory.

20. A network according to claim 14 wherein the processing unit event contains a freely programmable gate array (FPGA).

21. A tomographic system comprising:
a plurality of tomographic components configured to operate in combination with each other as a tomography apparatus;
a network for data and signal transmission among said plurality of tomographic components, each of said tomographic components having a network address in said network or another individual identification feature;
every tomographic component comprising a transmission unit configured to generate data packets to be sent via the data network and a reception unit configured to receive data packets at respective reception points in time and to process received data packets;
each transmission unit and each reception unit being configured to mutually synchronize the tomographic components according to the reception points in time, at the respective tomographic component, of received data packets and known transmission and processing times, and the transmission units are each configured to transfer the data packets synchronously in the data network;
each tomographic component comprising at least one mirror memory connected in parallel with a data input and/or output thereof, wherein at least a portion of the data packets that are incoming and outgoing via the data network is recorded in the mirror memory in parallel with the processing in the reception unit of that tomographic component;
at least one tomographic component comprising a processing unit that configured to detect a trigger event and that, upon detection of the trigger event, to freeze the mirror memory at said at least one tomographic component and to freeze the respective mirror memories of all other tomographic components located on the network to cause all of the respective mirror memories to contain data of the same time segment for respective different points of the data network; and
a transfer unit configured to transfer the data frozen in the mirror memories via the network while leaving the synchronized data traffic unaffected.

* * * * *